(12) United States Patent
Bissery

(10) Patent No.: US 6,664,242 B2
(45) Date of Patent: Dec. 16, 2003

(54) COMPOSITION AND METHOD COMPRISING CPT-11 AND A PYRIMIDINE DERIVATIVE FOR THE TREATMENT OF CANCER

(75) Inventor: Marie-Christine Bissery, Vitry sur Seine (FR)

(73) Assignee: Aventis Pharma S.A., Antony (FR)

( * ) Notice: Subject to any disclaimer, the term of this patent is extended or adjusted under 35 U.S.C. 154(b) by 78 days.

(21) Appl. No.: 10/032,489

(22) Filed: Jan. 2, 2002

(65) Prior Publication Data

US 2002/0091132 A1 Jul. 11, 2002

Related U.S. Application Data

(62) Division of application No. 09/793,520, filed on Feb. 27, 2001, now Pat. No. 6,503,889.
(60) Provisional application No. 60/208,938, filed on Jun. 5, 2000, and provisional application No. 60/185,378, filed on Feb. 28, 2000.

(51) Int. Cl.$^7$ .......................... A61K 31/70; A61K 31/44

(52) U.S. Cl. ......................... 514/49; 574/283

(58) Field of Search ........................ 514/283, 49, 258

(56) References Cited

U.S. PATENT DOCUMENTS

| 4,473,692 A | 9/1984 | Miyasaka et al. |
| 4,545,880 A | 10/1985 | Miyasaka et al. |
| 5,472,949 A | 12/1995 | Arasaki et al. |
| 5,889,017 A | 3/1999 | Giovanella et al. |
| 6,191,119 B1 | 2/2001 | Rubinfeld |

FOREIGN PATENT DOCUMENTS

| EP | 0 056 692 B1 | 7/1982 |
| EP | 0 074256 B1 | 3/1983 |
| EP | 0 088 642 A2 | 9/1983 |
| EP | 0 296 612 B1 | 12/1988 |
| EP | 0 321 122 B1 | 6/1989 |
| EP | 0 325 247 B1 | 7/1989 |
| EP | 0 540 099 B1 | 5/1993 |
| EP | 0 737 686 B1 | 10/1996 |
| JP | 57-116015 | 7/1982 |
| JP | 57-116074 | 7/1982 |
| JP | 59-5188 | 1/1984 |
| JP | 59-51289 | 3/1984 |
| JP | 60-19790 | 1/1985 |
| JP | 1-246287 | 10/1989 |
| JP | 1-249777 | 10/1989 |
| WO | WO 90/03169 | 4/1990 |
| WO | WO 96/37496 | 11/1996 |
| WO | WO 96/38146 | 12/1996 |
| WO | WO 96/38449 | 12/1996 |
| WO | WO 97/00876 | 1/1997 |
| WO | WO 01/30351 A1 | 5/2001 |

OTHER PUBLICATIONS

Bahadori et al., Anticancer Research (1999), 19(6B), 5423–5428 Abstract Only.*
Bahadori, H.R. et al., Proc. Am. Soc. Clin. Oncol., 17:477a (1998) AB:1837.
T.H. Corbett et al., "Evaluation of Single Agents and Combinations of Chemotherapeutic Agents in Mouse Colon Carcinomas," Cancer, 40(5):2660–2680 (1977).
T.H. Corbett et al., "Response of Transplantable Tumors of Mice to Anthracenedione Derivatives Alone and in Combination with Clinically Useful Agents," Cancer Treatment Reports, 66(5):1187–1200 (May 1982).
David L. Emerson et al., "In vivo Antitumor Activity of Two New Seven–substituted Water–soluble Camptothecin Analogues," Cancer Research, 55:603–609 (Feb. 1995).
Isabelle Madelaine et al., "Sequential Modifications of Topoisomerase I Activity in a Camptothecin–Resistant Cell Line Established by Progressive Adaptation," Biochemical Pharmacology, 45(2):339–348 (1993).
Abstract: Japio No. 00965715 for JP 57–116015.
Abstract: Japio No. 00965774 for JP 57–116074.
Abstract: Japio No. 01293588 for JP 59–5188.
Abstract: Japio No. 01541290 for JP 60–19790.
Abstract: Japio No. 02948687 for JP 1–246287.
Abstract: Japio No. 02952177 for JP 1–249777.
Abstract: Derwent No. 01984–110813/198418 for JP 59–051289.
Tomio Furuta and Teruo Yokokura, "Combination Therapy of CPT–11, a Camptothecin Derivative, with Various Antitumor Drugs Against L1210 Leukemia," Japanese Journal of Cancer and Chemotherapy, 18(3):393–402 (Mar. 1991); English Abstract p. 402.
M. Ise, C. Sakai, H. Tsujimura, K. Kumagai, T. Takenouchi and T. Takagi, "Sucessful Treatment with CPT–11 and Adriamycin for Hemophagocytic Syndrome Associated with Intravascular Lymphomatosis,"Jpn J. Clin. Hematology, 39(11):1131–1136, English Abstract p. 1136.
C. Sakai, T. Saotome, A. Takeshita, C. Nakaseko, K. Kumagai, and T. Takagi, "Irinotecan + Adriamycin QOL," Jpn. J. Cancer Chemotherapy 26(5):709–714 (1999); Chemical Abstract 115:21789.
Mirabelli, C.K., et al., "A Murine Model to Evaluate the Ability of in Vitro Clonogenic Assys to Predict the Response to Tumors in Vivo", Cancer Research, Official Journal of the American Association for Cancer Research, vol. 48, No. 19, pp. 5447–5454, Oct. 1, 1988.

\* cited by examiner

Primary Examiner—Jerome D. Goldberg
(74) Attorney, Agent, or Firm—Finnegan, Henderson, Farabow, Garrett, & Dunner LLP

(57) ABSTRACT

Therapeutic pharmaceutical compositions comprising a pyrimidine derivative in combination with camptothecin or a camptothecin derivative for the treatment of cancer are described. In one embodiment, the pyrimidine derivative is capecitabine and the camptothecin derivative is CPT-11.

6 Claims, No Drawings

COMPOSITION AND METHOD COMPRISING CPT-11 AND A PYRIMIDINE DERIVATIVE FOR THE TREATMENT OF CANCER

This application is divisional application of U.S. patent application Ser. No. 09/793,520, filed on Feb. 27, 2001, now U.S. Pat. No. 6,503,889 B2, which claims the benefit of U.S. provisional application No. 60/185,378, filed Feb. 28, 2000, and U.S. provisional application No. 60/208,938, filed on Jun. 5, 2000. These applications are relied upon for the benefits provided under 35 U.S.C. §§120 and 119, and the entire disclosures of these applications are incorporated herein by reference.

The present invention relates to therapeutic pharmaceutical compositions comprising an effective amount of a pyrimidine derivative in combination with an effective amount of camptothecin or camptothecin derivatives, which are useful for the treatment of cancer.

The invention relates to the treatment of cancer, especially solid tumors, with associations of camptothecin derivatives and other anticancer drugs and the use of such associations for an improved treatment.

More specifically, the invention relates to anticancer treatments with associations of camptothecin derivatives such as irinotecan (CPT-11; Camptosar®), topotecan, 9-aminocamptothecin and 9-nitrocamptothecin and a pyrimidine derivative. Pyrimidine derivatives include uracil, thymine, cytosine, methylcytosine and thiamine containing compounds. Examples of such pyrimidine derivatives are capecitabine, gemcitabine and multi-targeted antifolate (MTA), also known as pemetrexed.

European patent EP 137,145, incorporated herein, describes camptothecin derivatives of the formula:

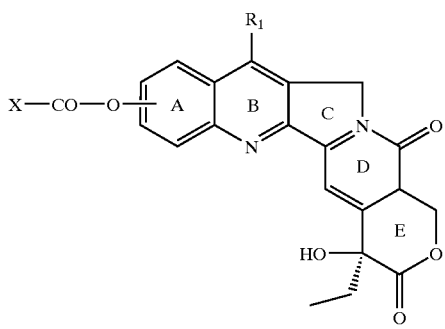

in which, in particular, $R_1$ is hydrogen, halogen or alkyl, X is a chlorine atom or $NR_2R_3$ in which $R_2$ and $R_3$, which may be identical or different, may represent a hydrogen atom, an optionally substituted alkyl radical, a carbocycle or a heterocycle which are optionally substituted, or alkyl radicals (optionally substituted) forming, with the nitrogen atom to which they are attached, a heterocycle optionally containing another hetero atom chosen from O, S and/or $NR_4$, $R_4$ being a hydrogen atom or an alkyl radical and in which the group X—CO—O— is located in position 9, 10 or 11 on ring A.

These camptothecin derivatives are anticancer agents which inhibit topoisomerase I, among which irinotecan, in which X—CO—O— is [4—(1-piperidino-1-piperidino] carbonyloxy, is an active principle which is particularly effective in treatment of solid tumors, and in particular, colorectal cancer.

The European patent application EP 74,256 also describes other camptothecin derivatives which are also mentioned as anticancer agents, in particular, derivatives of a structure analogous to the structure given above and in which X—CO—O— is replaced with a radical —X'R' for which X' is O or S and R' is a hydrogen atom or an alkyl or acyl radical.

Other camptothecin derivatives have also been described, for example, in the patents or patent applications EP 56,692, EP 88,642, EP 296,612, EP 321,122, EP 325,247, EP 540, 099, EP 737,686, WO 90/03169, WO 96/37496, WO 96/38146, WO 96/38449, WO 97/00876, U.S. Pat. No. 7,104,894, JP 57 116,015, JP 57 116,074, JP 59 005,188, JP 60 019,790, JP 01 249,777, JP 01 246,287 and JP 91 12070 or in Canc. Res., 38 (1997) Abst. 1526 or 95 (San Diego—12–16 April), Canc. Res., 55(3):603–609(1995) or AFMC Int. Med. Chem. Symp. (1997) Abst. PB-55 (Seoul—27 July–1 August).

Camptothecin derivatives are usually administered by injection, more particularly intravenously in the form of a sterile solution or an emulsion. Camptothecin derivatives, however, can also be administered orally, in the form of solid or liquid compositions.

CPT-11 is one of the most active new agents in colorectal cancer. Colorectal cancer is a leading cause of morbidity and mortality with about 300,000 new cases and 200,000 deaths in Europe and the USA each year (See P. Boyle, Some Recent Developments in the Epidemiology of Colorectal Cancer, pages 19–34 in *Management of Colorectal Cancer*, Bleiberg H., Rougier P., Wilke H. J., eds, (Martin Dunitz, London 1998); and—Midgley R. S., Kerr D. J., Systemic Adjuvant Chemotherapy for Colorectal Cancer, pages 126–27 in Management of Colorectal Cancer, Bleiberg H., Rougier P., Wilke H. J., eds, (Martin Dunitz, London 1998).) Although about fifty percent of patients are cured by surgery alone, the other half will eventually die due to metastatic disease, which includes approximately 25% of patients who have evidence of metastases at time of diagnosis.

In colorectal cancer patients resistant to 5-FU, single agent CPT-11 tested in two large phase III randomized trials resulted in a longer survival and a better quality of life compared with supportive care only (D. Cunningham, S. Pyrhönen, R D. James et al, The Lancet, 352 (9138):1413–1418 (1998)) and also in a longer survival without deterioration in quality of life compared with 5-FU/FA best infusional regimens (P. Rougier, E. van Cutsem et al; The Lancet, 352 (9138):1407–1418 (1998)). CPT-11 is therefore the reference treatment in metastatic colorectal cancer (MCRC) after failure on prior 5-FU treatment.

CPT-11 has also been shown to be at least as active as the so-called standard 5-FU/FA bolus in chemotherapy naive patients with MCRC [Proc. Am. Soc. Clin. Oncol., vol 13 (1994), (Abstr. #573); J. Clin Oncol, 14(3):709–715 (1996); J. Clin Oncol, 15(1):251–260 (1997).

Combinations of irinotecan (CPT-11) and 5-FU have already been studied in phase I studies in Japan, indicating in preliminary results that concurrent administration is feasible in terms of safety (L. Saltz et al., Eur. J. Cancer 32A, suppl 3:S24–31 (1996))

A study relating to CPT-11 published by D. Cunningham, Eur. J. Cancer, 32A suppl. 3:S1–8 (1996) concluded that CPT-11 offers a different cytotoxic approach that may complement the use of 5-FU/folinic acid in colorectal cancer.

To demonstrate the efficacy of a combination, it may be necessary to compare the maximum tolerated dose of the combination with the maximum tolerated dose of each of the separate constituents in the study in question. This efficacy may be quantified, for example by the $\log_{10}$ cells killed, which is determined by the following formula:

$$\log_{10} \text{ cell killed} = T\text{-}C(\text{days})/3.32 \times T_d$$

in which T-C represents the time taken for the cells to grow, which is the mean time in days for the tumors of the treated group (T) and the tumors of the treated group (C) to have reached a predetermined value (1 g for example), and $T_d$ represents the time in days needed for the volume of the tumor in the control animals (T. H. Corbett et al., Cancer, 40, 2660.2680 (1977); F. M. Schabel et al., Cancer Drug Development, Part B, Methods in Cancer Research, 17, 3–51, New York, Academic Press Inc. (1979)). A product is considered to be active if the $\log_{10}$ cell kill is greater than or equal to 0.7. A product is considered to be very active is the $\log_{10}$ cell kill is greater than 2.8.

The efficacy of a combination may also be demonstrated by determination of the therapeutic synergy. A combination manifests therapeutic synergy if it is therapeutically superior to one or the other of the constituents used at its optimum dose (T. H. Corbett et al., Cancer Treatment Reports, 66, 1187 (1982)).

It has now been found that the combination of camptothecin derivatives with pyrimidine derivatives is especially effective in the treatment of solid tumors, such as ovarian, NSCLC and colorectal cancer. Among the effective pyrimidine derivatives are gemcitabine, MTA, and capecitabine.

Gemcitabine exhibits antitumor activity. The salt of gemcitabine, 2'-deoxy-2',2'-difluorocytidine monohydrochloride, is provided for clinical use as an intravenous solution for treatment of solid tumors such as non-small cell lung cancer (NSCLC).

Gemcitabine exhibits cells phase specificity, primarily killing cells undergoing DNA synthesis (S-phase) and also blocking the progression of cells through the G1/S-phase boundary. Gemcitabine is metabolized intracellularly by nucleoside kinases to the active diphosphate (dFdCDP) and triphosphate (dFdCTP) nucleosides. The cytotoxic effect of gemcitabine is attributed to a combination of two actions of the diphosphate and the triphosphate nucleosides, which leads to inhibition of DNA synthesis. First, gemcitabine diphosphate inhibits ribonucleotide reductase, which is responsible for catalyzing the reactions that generate the deoxynucleoside triphosphates for DNA synthesis. Inhibition of this enzyme by the diphosphate nucleoside causes a reduction in the concentrations of deoxynucleotides, including dCTP. Second, gemcitabine triphosphate competes with dCTP for incorporation into DNA. The reduction in the intracellular concentration of dCTP (by the action of the diphosphate) enhances the incorporation of gemcitabine triphosphate into DNA (self-potentiation). After the gemcitabine nucleotide is incorporated into DNA, only one additional nucleotide is incorporated into DNA. After this addition, there is inhibition of further DNA synthesis.

Gemcitabine has shown promise in combination with CPT-11 as a treatment for pancreatic cancer in Phase II studies.

MTA (multi-targeted antifolate) is an antimetabolite which is a folate antagonist, dihydrofolate reductase inhibitor and thymidylate synthase inhibitor. It is provided for use as an intravenous solution and has been found to inhibit tumor growth in mice. It is currently being tested in humans for treatment of non-small lung cancer, mesothelioma, melanoma, bladder cancer, breast cancer, pancreatic cancer, colorectal cancer, and other solid tumors.

Capecitabine is a fluoropyrimidine carbamate with antineoplastic activity. It is an orally administered prodrug of 5'-deoxy-5-fluorouridine (5'-DFUR) which is converted to 5-fluorouracil in the body. In preclinical studies, capecitabine has demonstrated activity in colorectal, breast, and head and neck carcinomas, including those resistant to 5-FU.

The chemical name for capecitabine is 5'-deoxy-5-fluoro-N-[(pentyloxy)-carbonyl]-cytidine and it has a molecular weight of 359.35. Capecitabine has the following structural formula:

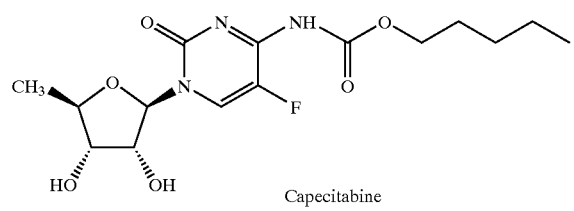

Capecitabine

Capecitabine has a unique mechanism of activation that exploits the high concentrations of the enzyme thymidine phosphorylase in tumor tissue compared with healthy tissue, leading to tumor-selective generation of 5-FU.

Two randomized, phase III studies have shown that oral capecitabine is an effective first-line therapy for metastatic colorectal cancer, achieving a superior response rate and at least equivalent survival and time to disease progression compared with intravenous (i.v.) 5-FU/leucovorin (Mayo Clinic regimen). Capecitabine also demonstrated a more favourable safety profile compared with the Mayo Clinic regimen.

The present invention is illustrated, but not limited, by the examples below.

EXAMPLE 1

The administration of oral CPT-11 and oral capecitabine, alone and together, was evaluated against the human colon carcinoma strain HCT-116 implanted in Swiss-nude mice. When the two compounds were co-adminstered, they were given one hour apart, with CPT-11 being given first. The volume of administration of each compound was 0.2 ml p.o. The table below shows that the maximum tolerated doses of both the single agents and the combined compounds were highly active.

TABLE 1

CPT-11/Capecitabine Simultaneous Oral Combination in HCT-116 Bearing Mice

| Agent | Daily Dosage (mg/kg/adm) | Schedule (Days) | $\log_{10}$ cell Kill | T-C (days) | Comments |
|---|---|---|---|---|---|
| CPT-11 | 80 | 5–9, 12–16 | — | — | Toxic |
| CPT-11 | 48 | " | | | HNTD highly active |
| CPT-11 | 29 | " | 2.1 | 30.1 | Active |
| capecitabine | 1860 | 5–9, 12–16 | | | Toxic |
| capecitabine | 1150 | 5–9, 12–16 | | | HNTD highly active |
| capecitabine | 713 | 5–9, 12–16 | 2.6 | 38.7 | Active |
| capecitabine | 443 | " | 1.1 | 16.3 | Active |
| CPT-11 + Capecitabine | 28.8 617 | 5–9, 12–16 | — | — | Toxic |
| CPT-11 + | 21.6 | " | 2.7 | 39.8 | HNTD |

TABLE 1-continued

CPT-11/Capecitabine Simultaneous
Oral Combination in HCT-116 Bearing Mice

| Agent | Daily Dosage (mg/kg/adm) | Schedule (Days) | Log$_{10}$ cell Kill | T-C (days) | Comments |
|---|---|---|---|---|---|
| Capecitabine | 463 | | | | highly active |
| CPT-11 + Capecitabine | 14.4 308 | " | 2.2 | 32.4 | Active |

HNTD: Highest Non-Toxic Dose; T-C Tumor Growth Delay

These results indicated that other schedules could optimize the combination and indeed, Example 2 below shows that the semi-simultaneous administration of capecitabine and CPT-11 results in a therapeutic combination that is very active against the tumor tested; that is, the capecitabine/CPT-11 combination gave a log$_{10}$ cell kill value of greater than 2.8.

EXAMPLE 2

The co-administration of oral CPT-11 and oral capecitabine was evaluated in Swiss-nude mice bearing early stage HCT-116 colon carcinoma. Three dosage levels of CPT-11 were given alone on days 18–22 to establish the highest non-toxic dose. Three dosage levels of capecitabine were given alone on days 18–22 and 25–29. In the combination arm, two semi-simultaneous schedules were investigated. The first schedule involved administering 4 dosage levels of CPT-11 on days 18–22 with administration of 4 dosage levels of capecitabine on days 18–22 and 25–29. In the second schedule, capecitabine was administered first on days 18–22, followed by simultaneous administration with 4 dosage levels of CPT-11 on days 25–29.

The two combined sequences were found to be as active as the best single agent and 42% and 55% of the highest non toxic dose of each single agent could be administered without overlap in host toxicity. The order of administration appeared to induce a difference in tolerance of the combined drugs. When capecitabine was administered first, the result seemed less toxic and was better tolerated than when CPT-11 was administered first. In both modes of administration, however, the efficacy of the combination remained the same.

The results obtained in the study of single agents CPT-11 and capecitabine and the combination of CPT-11/capecitabine are given below in the following table. Three combinations were very active with a log cell kill of greater than 2.8.

TABLE 2

CPT-11/Capecitabine Semi-Simultaneous
Oral Combination in HCT-116 Bearing Mice

| Agent | Daily Dosage (mg/kg/adm) | Schedule (Days) | Log$_{10}$ cell Kill | T-C (days) | Comments |
|---|---|---|---|---|---|
| CPT-11 | 155 | 18–22 | — | — | Toxic |
| CPT-11 | 96 | 18–22 | 1.7 | 21.3 | HNTD highly active |
| CPT-11 | 60 | 18–22 | 1.7 | 21.4 | Active |
| capecitabine | 1150 | 18–22 & 25–29 | 3.2 | 39.4 | HNTD highly active |
| capecitabine | 713 | 18–22 & 25–29 | 2.1 | 25.2 | Active |
| capecitabine | 443 | 18–22 & 25–29 | 2.1 | 26.1 | Active |
| CPT-11 + capecitabine | 72 771 | 18–22 18–22 & 25–29 | — | — | Toxic |
| CPT-11 + capecitabine | 57.6 617 | 18–22 18–22 & 25–29 | — | — | Toxic |
| CPT-11 + capecitabine | 43.2 771 | 18–22 18–22 & 25–29 | 3.4 | 41.7 | HNTD highly active |
| CPT-11 + capecitabine | 28.8 308 | 18–22 18–22 & 25–29 | 2.3 | 27.7 | Active |
| capecitabine CPT-11 + | 771 67.2 | 18–22 & 25–29 25–29 | — | — | Toxic |
| capecitabine CPT-11 + | 617 54.2 | 18–22 & 25–29 25–29 | 3.1 | 38.6 | HNTD highly active |
| capecitabine CPT-11 + | 463 38.1 | 18–22 & 25–29 25–29 | 3.3 | 40.0 | Highly active |
| capecitabine CPT-11 + | 308 25.2 | 18–22 & 25–29 25–29 | 2.3 | 28.1 | Active |

HNTD: Highest Non-Toxic Dose; T-C: Tumor Growth Delay

EXAMPLE 3

The safety and efficacy of two schedules of irinotecan (CPT-11) administered in combination with the standard dose of intermittent capecitabine were studied in patients with advanced/metastatic colorectal cancer.

The primary objective of the study was to compare the safety profiles of the treatment schedules. The secondary objective was to compare tumour response rates in the two treatment arms.

Patients received irinotecan i.v. 300/mg/m in one of two dose schedules in combination with intermittent, oral capecitabine in a 21-day treatment cycle (FIGS. 1 and 2).

FIGURE 1

Treatment schedule for arm A.

| | Day | | | |
|---|---|---|---|---|
| | 1 | 8 | 15 | 21 |
| Irinotecan 300 mg/m as a 90-minute i.v. infusion | ↑ | | | |
| Oral capecitabine 1.250 mg/m twice daily | | Days 2–15 | | |

FIGURE 2

Treatment schedule for arm B.

| | Day | | | |
|---|---|---|---|---|
| | 1 | 8 | 15 | 21 |
| Irinotecan 150 mg/m as a 90-minute i.v. infusion | ↑ | ↑ | | |

FIGURE 2-continued

Treatment schedule for arm B.

| | Day | | | |
|---|---|---|---|---|
| | 1 | 8 | 15 | 21 |
| Oral capecitabine 1.250 mg/m twice daily | | Days 2–15 | | |

A total of 19 patients with untreated or pretreated advanced colorectal cancer were enrolled in this pilot study. Treatment was administered until disease progression occurred or for a maximum of 10 treatment cycles in patients with tumour response or stable disease.

Patients with measurable, advanced or metastatic colorectal adenocarcinoma were eligible for enrollment. These included patients aged 18–75 years, with a life expectancy of at least 3 months and ECOG performance status 0–2. Patients aged 70–75 years were required to have ECOG performance status 0–1.

The baseline characteristics of the 19 patients are shown in Table 3.

TABLE 3

Patient characteristics.

| | No. of patients |
|---|---|
| Treatment arm A | 10 |
| Treatment arm B* | 9 |
| Male/female | 11/8 |
| Median age (years) [range] | 56[33–70] |
| Primary tumour | |
| Colon | 13 |
| Rectal | 6 |
| No prior chemotherapy | 9 |
| Prior chemotherapy+ | |
| Adjuvant setting | 6 |
| Metastatic setting | 5 |
| Metastatic sites | |
| Liver | 15 |
| Lung | 4 |
| Locally relapsing tumor | 2 |
| Primary tumor | 3 |

*One patient in treatment arm B died (not related to treatment) after receiving two treatment cycles
+One patient received treatment in both settings Safety was evaluated in all patients who received at least one dose of study medication, with adverse events graded according to National Cancer Institute Common Toxicity Criteria (NCI CTC). Hand-foot syndrome was graded 1–3. Tumours were assessed by investigators at baseline and at 9-weekly intervals based on World Health Organization criteria. The incidence of treatment-related adverse events in the 19 patients treated to date is shown in Table 4. There were no grade 4 treatment-related adverse events. Only one patient required dose modification for the management of toxicities.

TABLE 4

Incidence of treatment-related adverse events.

| | No. of patients | |
|---|---|---|
| | Treatment arm A (n = 10) | Treatment arm B (n = 9) |
| Diarrhoea | | |
| Grade 2 | 4 | 4 |
| Neutropenia | | |
| Grade 2 | 3 | — |
| Grade 3 | — | 2 |
| Hand-foot syndrome | | |
| Grade 2 | 4 | 3 |
| Grade 3 | 1 | — |
| Nausea | | |
| Grade 3 | — | 1 |

Eighteen patients were evaluable for response (Table 5).

TABLE 5

Antitumor activity of capecitabine/irinotecan combination regiments in patients with advanced/metastatic colorectal cancer

| | No. of patients | |
|---|---|---|
| Tumor response | Treatment arm A (n = 10) | Treatment arm B (n = 8) |
| Partial | 8 | 5 |
| Stable disease | 2 | 1 |
| Progressive disease | 0 | 2 |

These preliminary data show that the two 21-day regimens combining intermittent, oral capecitabine with i.v. irinotecan 300 mg/m administered in a single dose (day 1) or divided into two equal doses (days 1 and 8) have favorable safety profiles and show encouraging antitumour activity in patients with advanced metastatic colorectal cancer. Of the 10 patients in arm A, 8 had partial responses and 2 were stabilized. None showed progressive disease.

Thus, the combination of CPT-11 and the pyrimidine derivative, capecitabine, results in a very active combination for the treatment of cancer, such as colorectal cancer.

What is claimed is:

1. A synergistic therapeutic pharmaceutical combination comprising an effective amount of CPT-11 in combination with an effective amount of capecitabine, wherein the combination provides a synergistic effect in the in vivo treatment of cancer sensitive to said combination.

2. A method of treating a cancer by administering to a patient having said cancer a synergistic combination of CPT-11 and capecitabine, wherein said combination provides a synergistic effect in the in vivo treatment of cancer sensitive to said combination.

3. The method of claim 2, wherein CPT-11 and capecitabine are administered semi-simultaneously.

4. The method of claim 2, wherein CPT-11 and capecitabine are administered separately.

5. The method of claim 2, wherein CPT-11 and capecitabine are administered simultaneously.

6. The method of claim 2, wherein said cancer is colon cancer.

* * * * *